United States Patent
Ng et al.

(10) Patent No.: US 10,775,284 B2
(45) Date of Patent: Sep. 15, 2020

(54) METHOD OF EVAPORATING LIQUID IN MICRO-CAPILLARIES

(71) Applicant: JN Medsys Pte Ltd, Singapore (SG)

(72) Inventors: Kian Kok Johnson Ng, Singapore (SG); Koon Kiat Teu, Singapore (SG); Mei Tze Belinda Ling, Singapore (SG); Jia Wen Sim, Singapore (SG)

(73) Assignee: JN Medsys Pte Ltd, Singapore (SG)

( * ) Notice: Subject to any disclaimer, the term of this patent is extended or adjusted under 35 U.S.C. 154(b) by 234 days.

(21) Appl. No.: 15/576,851

(22) PCT Filed: May 26, 2016

(86) PCT No.: PCT/SG2016/050248
§ 371 (c)(1),
(2) Date: Nov. 27, 2017

(87) PCT Pub. No.: WO2016/190817
PCT Pub. Date: Dec. 1, 2016

(65) Prior Publication Data
US 2018/0172565 A1    Jun. 21, 2018

(30) Foreign Application Priority Data

May 27, 2015  (SG) .......................... 10201504170U

(51) Int. Cl.

| | |
|---|---|
| *C12P 19/34* | (2006.01) |
| *G01N 1/40* | (2006.01) |
| *B01L 3/00* | (2006.01) |
| *G01N 35/10* | (2006.01) |
| *C12Q 1/6848* | (2018.01) |
| *C12Q 1/686* | (2018.01) |
| *G01N 35/00* | (2006.01) |

(52) U.S. Cl.
CPC .............. *G01N 1/40* (2013.01); *B01L 3/5082* (2013.01); *B01L 3/50857* (2013.01); *C12Q 1/686* (2013.01); *C12Q 1/6848* (2013.01); *G01N 35/10* (2013.01); *B01L 2200/06* (2013.01); *B01L 2200/141* (2013.01); *B01L 2200/16* (2013.01); *B01L 2300/043* (2013.01); *B01L 2300/0832* (2013.01); *B01L 2300/0838* (2013.01); *B01L 2400/0406* (2013.01); *B01L 2400/049* (2013.01); *G01N 2035/00277* (2013.01)

(58) Field of Classification Search
None
See application file for complete search history.

(56) References Cited

U.S. PATENT DOCUMENTS

| | | | | |
|---|---|---|---|---|
| 6,033,880 | A * | 3/2000 | Haff ..................... | B01J 19/0046 422/50 |
| 6,794,127 | B1 * | 9/2004 | Lafferty ............... | B01J 19/0046 435/183 |
| 2003/0013115 | A1 * | 1/2003 | Lafferty ............. | G01N 21/0303 435/6.11 |
| 2003/0124599 | A1 * | 7/2003 | Chen .................... | B01J 19/0046 506/39 |
| 2003/0138941 | A1 | 7/2003 | Gong et al. | |
| 2005/0056205 | A1 | 3/2005 | Goodwin, Jr. | |
| 2005/0229841 | A1 * | 10/2005 | Redden .................... | C30B 7/00 117/68 |
| 2009/0288710 | A1 | 11/2009 | Viovy et al. | |
| 2010/0137152 | A1 * | 6/2010 | Gorfinkel ............ | B01L 3/50851 506/9 |
| 2011/0152108 | A1 * | 6/2011 | Brenan .................. | C12Q 1/686 506/7 |

OTHER PUBLICATIONS

Communication Pursuant to Article 94(3) EPC dated Oct. 16, 2019 From the European Patent Office Re. Application No. 16 800 398.6. (5 Pages).
Notification of Office Action and Search Report dated Apr. 14, 2020 From the China National Intellectual Property Administration of the People's Republic of China Re. Application No. 201680038154.7 and Its Translation (of Office Action) Into English. (19 Pages).
Notification of Office Action and Search Report dated Oct. 25, 2019 From the China National Intellectual Property Administration of the People's Republic of China Re. Application No. 201680038154.7 and Its Translation (of Office Action) Into English. (22 Pages).
Supplementary European Search Report and the European Search Opinion dated Oct. 25, 2018 From the European Patent Office Re. Application No. 16800398.6. (8 Pages).

* cited by examiner

*Primary Examiner* — Kenneth R Horlick

(57) ABSTRACT

There is provided a method of charging an array of micro-capillaries. The micro-capillaries have at least one end that is open for fluid communication. The method includes the steps of: (a) filling the array of micro-capillaries with an assay liquid; (b) controllably evaporating at least some of the assay liquid to remove it from the micro-capillary and create a void space in each of the capillaries between the assay liquid and the open end; and (c) filling the void space with a liquid that is immiscible with said assay liquid. There is also provided a use of the disclosed method and a device for charging an array of micro-capillaries.

13 Claims, 3 Drawing Sheets

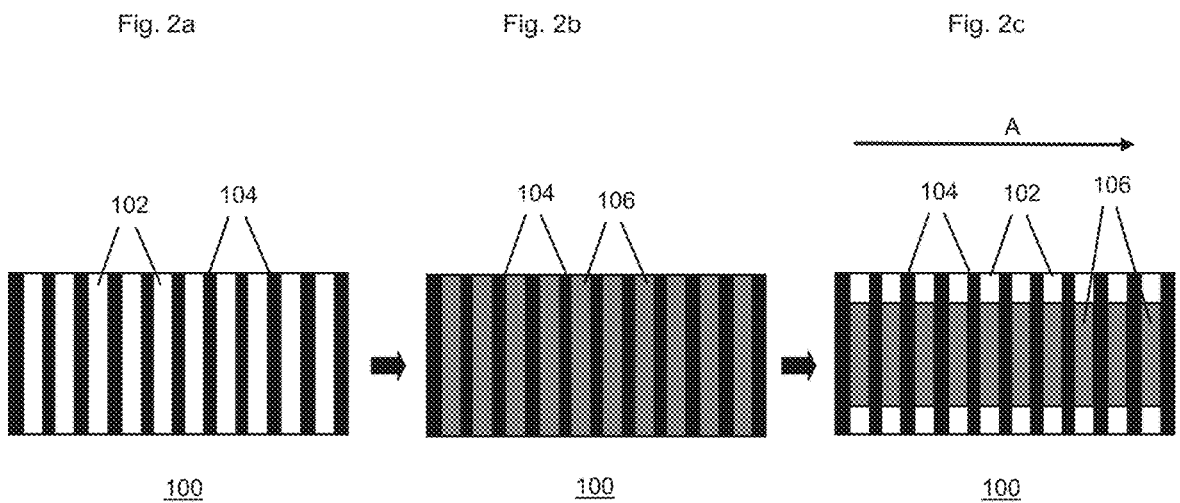
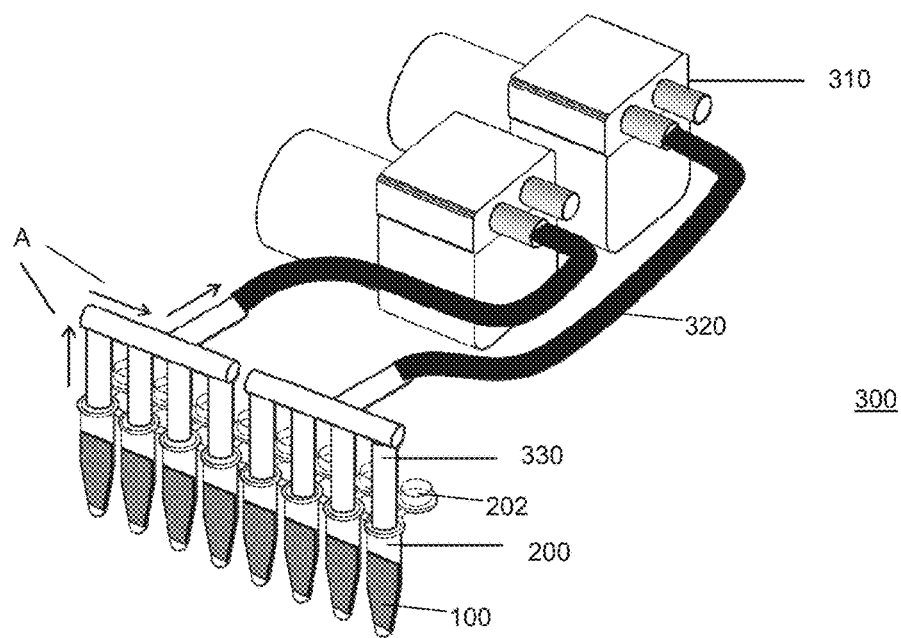

METHOD OF EVAPORATING LIQUID IN MICRO-CAPILLARIES

TECHNICAL FIELD

The present invention relates broadly, but not exclusively, to methods and devices for evaporating a liquid, and to methods and devices for isolating liquid samples.

BACKGROUND ART

In biochemical analyses, it is desirable to perform many reactions, sometimes ranging from hundreds to thousands to even tens of thousands, of biological samples in parallel. One way to perform a plurality of reactions in parallel is to use high-density plates or arrays containing many sample wells. High-density microplates are plates, or trays, used for running biological or biochemical tests, with many individually separate sites configured as separate wells per each plate, wherein each well can be used for a separate test. The number of wells on the plates can be 96 wells, 384 wells, 864 wells, 1536 wells or more. The plates may also have no physically separate wells, in which case, the plates can be flat plates with discrete or indiscrete deposit sites.

In other applications such as digital polymerase chain reactions (PCR), the sample assay is partitioned into sub-reactions. One effective way to do that is to use a high-density array comprising thousands of open-ended sample wells. Typically, the wells are packed very close together. The dividing wall between adjacent wells can have a thickness ranging from 1 μm to 100 μm.

In general, after the wells have been filled with respective sample assays, the assays are sealed within the wells using a compatible immiscible liquid, such as mineral oil. Normally, that would be sufficient to isolate the reactions in the sample assays and prevent them from interacting with one another. However, when the array is subjected to heating, such as in a thermal cycling process common in PCR, sealing by a mineral oil layer may be ineffective in isolating the assays in the respective wells. For example, heating might cause the assays to expand out of the wells, and thus create contact between adjacent assays. The presence of air gaps, particularly at the oil-assay interface, may exacerbate the problem, since air expands faster when heated and may then push the assay out of the well. If the surfaces of the array are hydrophilic, there is also a higher tendency for the assays to flow out of the respective wells when heated. Any liquid not capped with the mineral oil layer may easily exit a micro-capillary, spill over onto an open end of an adjacent well and be drawn into the adjacent well.

It is desirable for the individual assays in the high-density array to be discrete and isolated from one another, particularly during a heating process where there is a strong tendency for assays to expand and interact with adjacent assays. When the assays are allowed to physically contact one another during a biochemical process, erroneous results such as false positives may occur.

Cross-contamination of samples can be prevented by increasing the separation between adjacent samples. In current techniques, wells are pre-fabricated so that there is sufficient spacing between them. However, such arrays have reduced well densities.

Thus, there is a need to provide a method and device for isolating liquid samples that overcome, or at least ameliorate, one or more of the disadvantages described above.

SUMMARY OF INVENTION

In a first aspect, there is provided a method of charging an array of micro-capillaries, the micro-capillaries having at least one end that is open for fluid communication, the method comprising the steps of: (a) filling the array of micro-capillaries with an assay liquid; (b) controllably evaporating at least some of the assay liquid to remove it from the micro-capillary and create a void space in each of the capillaries between the assay liquid and the open end; and (c) filling the void space with a liquid that is immiscible with said assay liquid.

In a second aspect, there is provided the use of the method as disclosed herein in a method of conducting a polymerase chain reaction.

In a third aspect, there is provided a device for charging an array of micro-capillaries, the device comprising: a holder containing the array of micro-capillaries, wherein the micro-capillaries have at least one end that is open for fluid communication; and a pumping means in fluid communication with the holder, wherein the pumping means is operable to controllably evaporate at least some of the assay liquid to create a void space in each of the capillaries between the assay liquid and the open end.

BRIEF DESCRIPTION OF DRAWINGS

Embodiments of the invention will be better understood and readily apparent to one of ordinary skill in the art from the following written description, by way of example only, and in conjunction with the drawings, in which:

FIG. 1b shows a schematic diagram of a perspective view of the plurality of holders shown in FIG. 1a.

FIG. 1c shows a schematic diagram of a side view of a holder shown in FIG. 1a.

FIGS. 2a-2c show schematic diagrams of a cross-sectional view of a micro-capillary array during various steps of an evaporation method in accordance with an example embodiment of the present disclosure.

FIG. 3 shows a schematic diagram of a device for evaporating a liquid contained in a closely packed array of micro-capillaries in accordance with an embodiment of the present disclosure.

BRIEF DESCRIPTION OF DRAWINGS

Figure 1A:
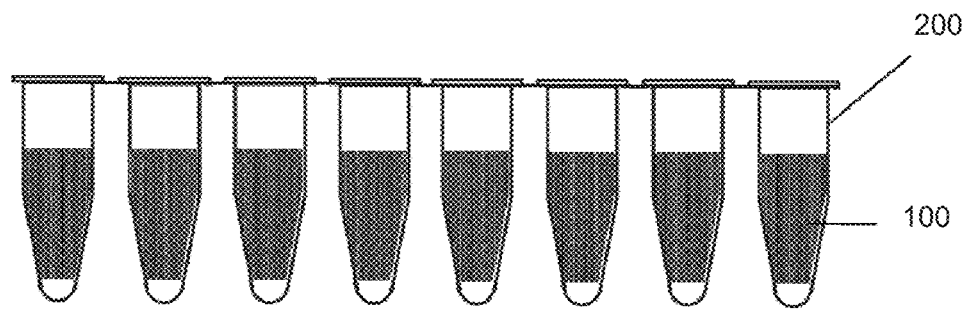
FIG. 1a shows a schematic diagram of a front view of a plurality of holders each housing a high-density array in accordance with an embodiment of the present disclosure.

In an example embodiment, a method of conducting a polymerase chain reaction includes charging an array of micro-capillaries comprising: filling an array of micro-capillaries with a polymerase chain reaction assay; controllably evaporating at least some of the assay to remove it from the micro-capillary and create a void space in each of said capillaries between the assay and the open end; filling the void space with a liquid that is immiscible with said assay contained in the micro-capillaries; and heating the array of micro-capillaries. The method and device for charging an array of micro-capillaries will be described in more detail below.

It is imperative for any type of assays performed in an array to yield results that are as accurate as possible. The assays entail, for example, qualitatively assessing or quantitatively measuring the amount or the functional activity of a target analyte in a sample obtained from an organism. Exemplary assays may include biological, chemical or biochemical assays. Exemplary assays may include cell assays, protein assays, gene expression analyses, genotyping assays and microRNA (miRNA) analyses. In many of these assays, the target analyte may be required in large quantities for analysis. Accordingly, amplification of the target analyte may be required during an assay.

The liquid contained in the micro-capillary or array of micro-capillaries may be in the form of a solution or a suspension. The liquid may comprise components capable of chemically reacting with each other. The reactive components or reactants depend on the assay performed. For example, in a fluorescent ligand binding assay, the liquid may comprise a biological sample obtained from an organism, a receptor that binds to a target analyte that may be present in the biological sample and a fluorescent detection molecule is capable of binding to the target analyte/receptor complex. The liquid may comprise assay reagents. In a particular embodiment, the liquid may comprise reagents suitable for use in a polymerase chain reaction assay.

Assays generally involve many reactions, such as the amplification reactions described above. It may thus be advantageous to perform many reactions in parallel. In a simplified example, a urine sample obtained from a human is to be analyzed for presence of five target proteins. Accordingly, the sample may be reacted with five separate reagents to determine whether the target proteins are present or absent. As may be appreciated, it would be advantageous to perform these reactions in parallel to save time, thereby saving cost.

An array comprising a plurality of micro-capillaries is typically used to perform a plurality of reactions in parallel. The array of micro-capillaries may be a closely packed array of micro-capillaries or a high density array of micro-capillaries.

A suitable array of micro-capillaries is described in WO2014/058393. Typically, the micro-capillaries are filled with liquid or assay. For example, the liquid can be provided onto the liquid receiving surface of the array, for example, by means of a pipette. Capillary action of the micro-capillaries may then draw the liquid in to fill the entire micro-capillary. Accordingly, the liquid is partitioned into individual micro-capillaries, each micro-capillary or group of capillaries denoting an individual reaction.

Each micro-capillary may be open at one or both ends. Thus, when packed together, the array of micro-capillaries forms the liquid receiving surface on one or both ends of the array, as the case may be. In embodiments, the micro-capillaries are configured to have geometries that draw liquid provided on a liquid receiving surface into the micro-capillary through capillary action. In embodiments, the geometries of the micro-capillaries are configured to permit liquid drawn into the micro-capillary to be retained within the micro-capillary due to the surface tension of the liquid and adhesive forces between the liquid and walls of the micro-capillary.

Removing liquid contained in micro-capillaries by natural evaporation may take a long time, e.g. more than 10 minutes or even hours, due to the forces involved. Hence, naturally evaporating liquid contained in micro-capillaries is impractical when the array is used in assays such as biochemical analysis.

Embodiments relating to methods and devices for charging an array of micro-capillaries will now be described in detail below.

There is provided a method of charging an array of micro-capillaries, said micro-capillaries having at least one end that is open for fluid communication, the method comprising the steps of: (a) filling the array of micro-capillaries with an assay liquid; (b) controllably evaporating at least some of the assay liquid to remove it from the micro-capillary and create a void space in each of said capillaries between the assay liquid and the open end; and (c) filling the void space with a liquid that is immiscible with said assay liquid.

The evaporating step (b) provides a way to rapidly evaporate liquid contained in the micro-capillaries. The array of micro-capillaries may be subject to the evaporating step (b) as disclosed herein to rapidly evaporate a predetermined portion of the assay liquid contained in the micro-capillaries. The evaporation process may be performed during the filling step (a) or after the filling step (a). In an embodiment, the evaporation process is performed after the filling step (a). In an embodiment, the array is placed into a holder and provided to the disclosed device to thereby controllably evaporate at least a predetermined portion of assay contained in the micro-capillaries.

In the above example embodiment, the method comprises filling the void space in the micro-capillaries between the assay liquid and the at least one open end with a liquid that is immiscible with the assay liquid. In an embodiment, the array may be removed from the disclosed device and immiscible liquid is provided onto the liquid receiving surface of the array, for example, by means of a pipette.

In the above example embodiment, the method comprises a heating step, e.g. a thermal cycling step of a polymerase chain reaction. Advantageously, because the assay is isolated within the micro-capillary by a thicker layer of immiscible liquid as compared to prior art assays, the heating step does not cause the assay to flow out of the micro-capillary and contact assays in adjacent micro-capillaries.

The above example method may be used in the operation of any device known in the art of polymerase chain reactions to carry out the polymerase chain reaction.

Figure 1B:
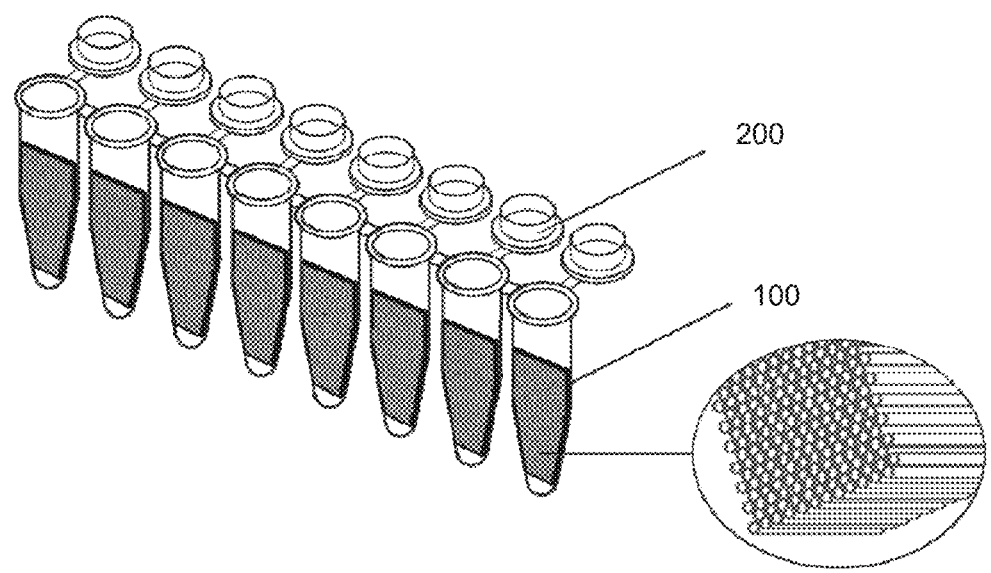
Figure 1C:
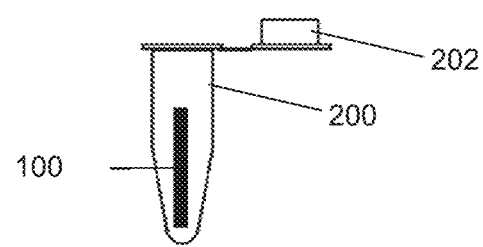

As described above, the array of micro-capillaries may be housed in a holder. FIGS. 1a to 1c show an example embodiment of the holder. FIG. 1a shows a schematic diagram of a front view of a plurality of holders 200 each housing a high-density array 100 in accordance with embodiments of the present disclosure. FIG. 1b shows a schematic diagram of a perspective view of the plurality of holders 200 shown in FIG. 1a. It can be seen from the inset of FIG. 1b that the high-density array 100 comprises micro-capillaries closely packed together. The side view of a holder 200 having a cap 202 and housing the high-density array 100 is shown in FIG. 1c.

The holder may be a container of suitable size to house the array. The holder may be a tube, such as an Eppendorf tube having a selectively sealable cap. An example holder is also described in WO2014/058393.

The term "array" as used in the present disclosure refers to a multiple number of capillaries that form a regular pattern, such as a grid pattern or a hexagonal pattern.

The term "capillary" as used in the present disclosure refers to a tube or channel or other structure that is capable of supporting a volume or column of liquid. The geometry of a capillary may vary widely and includes, but is not limited to, tubes with circular, rectangular or square cross-sections, channels, grooves, plates, and the like, and may be fabricated by a wide range of technologies. The term "micro-capillary" is construed accordingly, to refer broadly, unless specified, to an average capillary diameter of between about 1 µm to about 1000 µm.

It will be appreciated that the diameter and depth of each micro-capillary may vary as required. In some instances, the micro-capillary may have a diameter of about 10 µm to about 300 µm. The micro-capillary may have a depth of about 1 mm or more, or less than 1 mm, or at least about 50 µm. The micro-capillary may have a volume of about 0.1 nL to about 50 nL. A micro-capillary volume of as low as 0.01 nL is also envisioned.

Each micro-capillary may have any shape suitable for holding a liquid sample. Each micro-capillary may be in the form of a well or an open-ended well or a through-hole or a trench. Each micro-capillary or a group of micro-capillaries may be designated to perform a reaction different from the adjacent micro-capillary or adjacent group of micro-capillaries. Each reaction may require the same or different reactants and reagents. Reactants and/or reagents from the different reactions may react with each other to produce unrelated and/or inaccurate results. Reactants and/or reagents from the different reactions may contact or mix with each other to produce unrelated and/or inaccurate results. Accordingly, it is advantageous to seal off or isolate or discretize the individual reactions present in each micro-capillary of an array to prevent the liquid from crossing over and affecting or contaminating another reaction in an adjacent micro-capillary.

The micro-capillary is part of an array comprising a plurality of micro-capillaries. The array of micro-capillaries may be any type of array used for assays. For example, the array may be a micro-well array, a multi-well array, a multiplex array or a high-density array.

The term "closely packed" in relation to the array of micro-capillaries means the density of micro-capillaries in the array is more than a thousand micro-capillaries per $mm^2$ of array, or more than 5,000 micro-capillaries per $mm^2$ of array, or more than 10,000 micro-capillaries per $mm^2$ of array. In other instances, the term "closely packed" refers to an open area ratio, i.e. the total area of the micro-capillary openings of a liquid receiving surface over the total area of the liquid receiving surface, of about 60% to about 90%. In an embodiment, the micro-capillary or well density of the arrays that can be used in the present disclosure may range from about 10 wells/$mm^2$ of the array to about 12,000 wells/$mm^2$ of the array based on an open area ratio of 60-90% and well diameter of 10-300 µm. In yet other instances, the term "closely packed" refers to an array of micro-capillaries wherein the wall thickness between adjacent micro-capillaries is between about 1 µm and about 1000 µm. The term "closely packed array" is used interchangeably herein with the term "high-density array".

The array of the present disclosure may contain at least 200 or 500 or 5,000 or 10,000 or 100,000 micro-capillaries or wells. Consequently, the array can possibly include up to 200 or 500 or 5,000 or 10,000 or 100,000 different reactions, wherein each well involves one reaction.

As mentioned above, due to the various forces, such as capillary force, surface tension, etc, acting on the liquid contained in the micro-capillary, evaporation of the liquid rapidly, e.g. in less than 10 min, would require assistance. Accordingly, the evaporating step (b) may comprise controlling the rate of evaporation in step (b). The evaporating step (b) may comprise a step of passing a gas, such as air, over one or both open ends of the capillaries. In examples, the gas may be any gas that is substantially inert with the assay liquid, e.g. nitrogen or air.

The step of passing gas over the open end of the capillaries may be effected by a pumping means. The flow of gas may be laminar or turbulent. Pumping means may be provided in the example embodiments to control or, in certain instances, increase the rate of evaporation of the liquid. The pumping means may comprise a negative pressure pump or a positive pressure pump. The pumping means may comprise more than one pump.

The evaporating step (b) may comprise a step of pumping gas over the at least one open end of the capillaries by a positive pressure pump. The evaporating step (b) may comprise a step of pulling gas over the at least one open end of the capillaries by creating a vacuum with a negative pressure pump. In instances, the evaporating step (b) may comprise pulling and pumping gas over the at least one open end of the capillaries.

Several factors may affect the rate of evaporation including, for example, flow rate and moisture of air surrounding the liquid exposed to the air; pressure of the surroundings and/or the assay; surface area of the liquid exposed to the surroundings; temperature of the surroundings and/or the liquid; and the properties of the liquid.

In some embodiments, the rate of evaporation of the liquid is controlled, e.g. by controlling the flow rate of the air supplied/drawn by the pumping means. The timing and duration of evaporation of the liquid may be controlled so that evaporation occurs only when desired. The control of the conditions of evaporation may be executed by a user. The controlled evaporation advantageously ensures that the assay or reaction is performed without or with little compromise.

The controlled evaporation process may at least partially reduce the volume of the liquid in the micro-capillary. The controlled evaporation process may at least partially remove a portion of the liquid in the micro-capillary such that the volume of the liquid remaining in the micro-capillary is sufficient for reactions of an assay to take place. This ensures that the volumes in the micro-capillaries are maintained for reaction. The controlled evaporation process advantageously reduces the volume of the liquid in each micro-capillary so that the remaining liquid may not contact liquid in an adjacent micro-capillary. The controlled evaporation process advantageously creates more allowance for liquid to expand or move within the micro-capillary without exiting the micro-capillary. The controlled evaporation process advantageously creates a void space between the liquid in a micro-capillary and the opening of the micro-capillary, thereby reducing or eliminating contact of the liquid in adjacent micro-capillaries via the open ends.

In other words, the controlled evaporation process creates a gap or separation between adjacent samples, and in some embodiments, adjacent reactions. The controlled evaporation process effectively creates a larger gap between adjacent micro-capillaries to prevent cross-contamination without the need to decrease the number of micro-capillaries in an array. The void space or gap provides an effective barrier that helps to minimize the contact between two or more adjacent reactions of an assay particularly when the array is subjected to heating, such as in a thermal cycling process commonly used in polymerase chain reactions. The controlled evaporation process intentionally increases the separation between adjacent, discrete reactions by increasing the distance from the assay liquid to the open end(s) of the microcapillary. Accordingly, the disclosed methods do not require the use of customized arrays to increase the separation between adjacent reactions. The disclosed methods can advantageously utilize high density arrays and yet yield accurate results. Accuracy of the assay can be achieved without reducing the density of the micro-capillaries of an array.

Further advantageously, the step of evaporating at least some of the liquid in the micro-capillary is a non-contact step. That is, no further reagents are required to be added into the liquid to achieve a reduction in volume of the liquid contained in the micro-capillary. Furthermore, the liquid contained in the micro-capillary does not require contact with any additional equipment, in order for its removal to be effected. Advantageously, no further components that may affect the accuracy of downstream processes or methods are required to achieve the effect of the disclosed method.

In some embodiments, the evaporation process may be controlled such that a predetermined portion of liquid is evaporated from the micro-capillaries. The evaporating process may comprise removing up to about 50 vol % of the liquid contained in the micro-capillary. Depending on the requirements, about 45 vol % or about 40 vol % or about 35 vol % or about 30 vol % or about 25 vol % or about 20 vol % of the liquid contained in the micro-capillary may be removed.

In some embodiments, the passing step comprises controlling the flow rate of air over one or both open ends of the capillaries. The evaporation process may comprise a step of pumping air over the open end of the capillaries. The evaporation process may comprise a step of pulling air over the open end of the capillaries. The pumping means may be controlled to provide a flow rate of air over the liquid receiving surface. The flow of air may be laminar or turbulent. The controlling may comprise controlling the flow rate of air to be between 0.5 L/min and 50 L/min, or about 0.5 L/min to about 40 L/min, or about 0.5 L/min to about 30 L/min, or about 0.5 L/min to about 20 L/min, or about 1 L/min to about 50 L/min, or about 1 L/min to about 40 L/min, or about 1 L/min to about 30 L/min, or about 1 L/min to about 20 L/min, or about 5 L/min to about 50 L/min, or about 5 L/min to about 40 L/min, or about 5 L/min to about 30 L/min, or about 5 L/min to about 20 L/min, or about 10 L/min to about 40 L/min, or about 20 L/min to about 50 L/min. The Reynolds number of the air flow may be anywhere from about 200 to about 20,000, or about 200 to about 10,000, or about 200 to about 5,000, or about 200 to about 1,000, or about 500 to about 20,000, or about 1,000 to about 20,000, or about 5,000 to about 20,000, or about 500 to about 15,000, or about 500 to about 10,000, or about 1,000 to about 10,000. The flow rate of air may be varied during the course of operation of the pumping means. For example, the flow rate of air may be controlled to be faster at the start and slower towards the end.

The passing step may comprise controlling the duration of the passing step. The pumping duration of the pumping means may be controlled. The controlling may comprise controlling the duration to be between about 10 seconds and about 5 minutes, or about 10 seconds and about 4 minutes, or about 10 seconds and about 3 minutes, or about 10 seconds and about 2 minutes, or about 20 seconds and about 5 minutes, or about 20 seconds and about 4 minutes, about 20 seconds and about 3 minutes, or about 20 seconds and about 2 minutes, or about 30 seconds and about 5 minutes, or about 30 seconds and about 4 minutes, or about 30 seconds and about 3 minutes, or about 30 seconds and about 2.5 minutes, or about 30 seconds and about 2 minutes, or about 30 seconds and about 1.5 minutes, or about 1 minute and about 5 minutes, or about 1 minute and about 4 minutes, or about 1 minute and about 3 minutes, or about 1 minute and about 2.5 minutes, or about 1 minute and about 2 minutes, or about 1 minute and about 1.5 minutes.

The pumping means may provide air through an outlet of the pumping means, such as a nozzle. The disclosed method of evaporation may further include adjusting a distance of a nozzle of the pumping means from the liquid receiving surface. The nozzle is positioned at a distance from the liquid receiving surface to increase the rate of evaporation of the liquid contained in the micro-capillary. The nozzle is positioned to create an air flow above, at or around the at least one open end of the micro-capillary. Hence, the nozzle may be positioned to be in fluid communication with the liquid receiving surface of the array. In embodiments where the array is housed in a holder, the nozzle may be positioned to be in fluid communication with the holder housing the array, such that air flows into the holder and across the liquid receiving surface of the array in the holder. In embodiments where a plurality of holders is provided, a nozzle is provided to be in fluid communication with each holder.

The distance of a nozzle of the pumping means from the liquid receiving surface or the open end of the capillaries may be adjusted or controlled. For example, in a positive pressure pump, the nearer the source of air flow is to the liquid receiving surface, the faster the rate of evaporation. The source of air flow from such pumping means may be the nozzle of the pumping means.

The nozzle of the pumping means may be sized to provide a sufficient rate of evaporation for the purposes of the disclosed methods. In embodiments where the array is housed in a holder, the nozzle may be sized appropriately such that the nozzle can be inserted into an opening of the holder. For example, the nozzle may be sized to fit loosely into an opening of the holder.

It may be appreciated that other ways of increasing the rate of evaporation of the liquid are contemplated in the present disclosure. For example, heat may be used during the evaporation step to increase the rate of evaporation.

In the example embodiments, there is also provided a method of isolating a liquid contained in a micro-capillary from adjacent micro-capillaries in an array of micro-capillaries, the method comprising: controllably evaporating at least a predetermined portion of the liquid contained in the micro-capillary using the evaporation method as described above; filling the void space in the micro-capillary vacated by the evaporated liquid with an immiscible liquid.

The disclosed liquid isolation method may be used for reducing or preventing cross-contamination between liquids in adjacent micro-capillaries. Advantageously, the disclosed method aids in experiments or assays performed in an array, and in particular closely packed arrays, to yield results that are as accurate as possible. Advantageously, the disclosed method prevents cross-contamination when pressure within the micro-capillary builds up. Advantageously, the assay in each micro-capillary is sealed and made discrete from that of the adjacent micro-capillary. Thus, erroneous results arising from cross-contamination due to expansion of the liquid assay or expansion of air pockets in the micro-capillary can be reduced or prevented. Advantageously, rapid evaporation results in rapid enlargement of the gaps between adjacent reactions, and thus improves the isolation between reactions so that the subsequent heating step can quickly take place.

Each liquid contained in a micro-capillary may comprise the same or different components as the liquid contained in an adjacent micro-capillary. The liquid in a group of micro-capillaries may comprise the same or different components from the liquid in adjacent groups of micro-capillaries.

The immiscible liquid acts as a barrier that isolates the liquid contained in the micro-capillary from the surrounding or from adjacent micro-capillaries. Advantageously, the gaps or void spaces created by the evaporation step are filled with a liquid that is immiscible with the liquid remaining in the micro-capillary, thereby sealing the liquid within the micro-capillary.

The term "immiscible" refers to two fluids, e.g. liquids or gases or mixtures of both, which are completely insoluble in each other. However, the term "immiscible" as used herein does not exclude some degree of mutual solubility. A system of two immiscible fluids consists of two phases and may be referred to as a mixture. An example of an immiscible fluid suitable for an aqueous phase is mineral oil.

The immiscible liquid disclosed herein may completely or substantially completely displace the air in the gaps created by the evaporation step. Given the small dimensions of the array disclosed herein, introduction of air into the assay in the array presents significant operation problems and can cause the contents in the compartments of the array to be pushed out, resulting in cross-over reactions. Furthermore, purging the air from the assay and redoing the assay wastes time and valuable resources. Advantageously, the disclosed method can effectively purge air out of the filled micro-capillary, thereby preventing problems relating to the presence of air gaps in the assay.

The immiscible liquid may completely or substantially completely fill the spaces or gaps of the micro-capillary that are not filled with liquid. The immiscible liquid effectively seals off the liquid contained in the micro-capillary from the surrounding.

As some liquid contained with the micro-capillary is evaporated away, the immiscible liquid layer may be thicker than prior art methods that do not comprise a step of removing liquid before adding an immiscible liquid layer. The thicker immiscible liquid layer of the present disclosure advantageously provides a more effective barrier between adjacent micro-capillaries as compared to prior art assays.

A schematic diagram of the disclosed methods in accordance with an embodiment of the present disclosure is shown in FIGS. 2a to 2c.

In FIG. 2a, an empty high-density array 100 is provided. The high-density array 100 comprises a plurality of wells 102 separated by walls 104. The number of wells can be 96 wells, 384 wells, 864 wells, 1536 wells or more. The walls 104 dividing adjacent wells 102 can have thicknesses ranging from about 1 μm to about 100 μm.

Next, as shown in FIG. 2b, the wells 102 are filled with assay 106. The assay 106 can include biological or chemical species, for example, a gene or gene product from a biological organism. The assay 106 can also include reagents depending on the type of assay performed.

Further, as shown in FIG. 2c, a predetermined portion of the assay 106 is evaporated to create spaces in the wells 102. The portion of the assay 106 is evaporated by, for example, increasing the flow rate of air above the wells 102 in the direction of arrow A. The rate of evaporation of the assay 106 exposed to the air above the wells 102 can therefore be increased, to thereby effect the removal of a portion of the assay 106. The spaces in the wells 102 left behind from the removed portion of assay 106 can then be filled with immiscible liquid (not shown) to isolate and seal the assay 106 within each well 102.

The disclosed isolation method may thus be used in a method of conducting a polymerase chain reaction.

In the example embodiments, there is provided a device for charging an array of micro-capillaries, the device comprising: a holder containing the array of micro-capillaries, wherein said micro-capillaries have at least one end that is open for fluid communication; and a pumping means in fluid communication with the holder, wherein the pumping means is operable to controllably evaporate at least some of the assay liquid to remove it from the micro-capillary and create a void space in each of said capillaries between the assay liquid and the open end.

The device may comprise more than one holder, wherein each holder contains an array of micro-capillaries.

The pumping means may be operable to control the flow rate of air over the open end of the capillaries. The pumping means may be operable to control the duration of evaporation. The pumping means may be operable to remove up to about 50 vol % of the assay liquid from the capillaries, or as disclosed herein. The pumping means may be operable to control the flow rate of air to between about 0.5 and 50 L/min, or as disclosed herein. The pumping means may be operable to control the duration of evaporation to between about 30 seconds and 5 minutes, or as disclosed herein.

Advantageously, due to the ability to control the conditions affecting the rate of evaporation, the disclosed device can be used with any type of closely packed array of micro-capillaries for any suitable reaction or liquid assay.

Advantageously, the disclosed methods and devices provide a way to perform biochemical experiments that prevent, or at least reduce the possibility of, cross-over reactions that may result in erroneous results.

Embodiments disclosed herein may also apply to the disclosed device.

A schematic diagram of a device 300 for evaporating a liquid contained in a closely packed array of micro-capillaries in accordance with an embodiment of the present disclosure is shown in FIG. 3.

In FIG. 3, device 300 comprises a row of holders 200 having caps 202. Each holder 200 houses a high-density array 100. Device 300 also comprises one or more vacuum pumps 310 connected to holders 200 by conduits 320, such that vacuum pumps 310 are in fluid communication with holders 200. Conduits 320 branch out into nozzles 330 that fit loosely into the open ends of the holders 200. Although not shown in FIG. 3, it will be appreciated that vacuum pumps 310 may further include control circuits and associated components such as programmable logic controllers, microprocessors, memory, etc, which can control the operation of the vacuum pumps 310 based on a control regime selected by the user. Air flow generated by vacuum pumps 310 is indicated by arrows A. It may be appreciated that in alternate embodiments where positive pressure pumps are used, the air flow generated will be in the opposite direction as arrows A. In some embodiments, the holders 200 and vacuum pumps 310 may be provided as a kit. For example, the holder may be provided separately from the pump and the holder and pump can be assembled together to provide device 300.

In use, a user fits nozzles 330 into the open ends of holders 200. The user may lower nozzles 330 further into holders 200 or raise nozzles 330 above the open ends of holders 200, as desired. It may be appreciated that the placement of nozzles 330 may be automated.

In one embodiment, the operating parameters such as air flow rate, pumping duration, etc, are preset based on prior calibration. For example, if the same analyses are repeated, the operating parameters are fixed to maintain consistency and the user operates the pump 310 by pressing a single button. In another embodiment, several options such as "slow", "medium", "fast", or other appropriate options, may be pre-programmed and offered for selection by the user. In yet another embodiment, the user activates vacuum pumps 310 and inputs into a controller (not shown) the desired pumping duration and/or the desired flow rate of air before running the vacuum pumps 310. Various other control regimes exist, and the above examples are just for illustration only.

Figure 4:
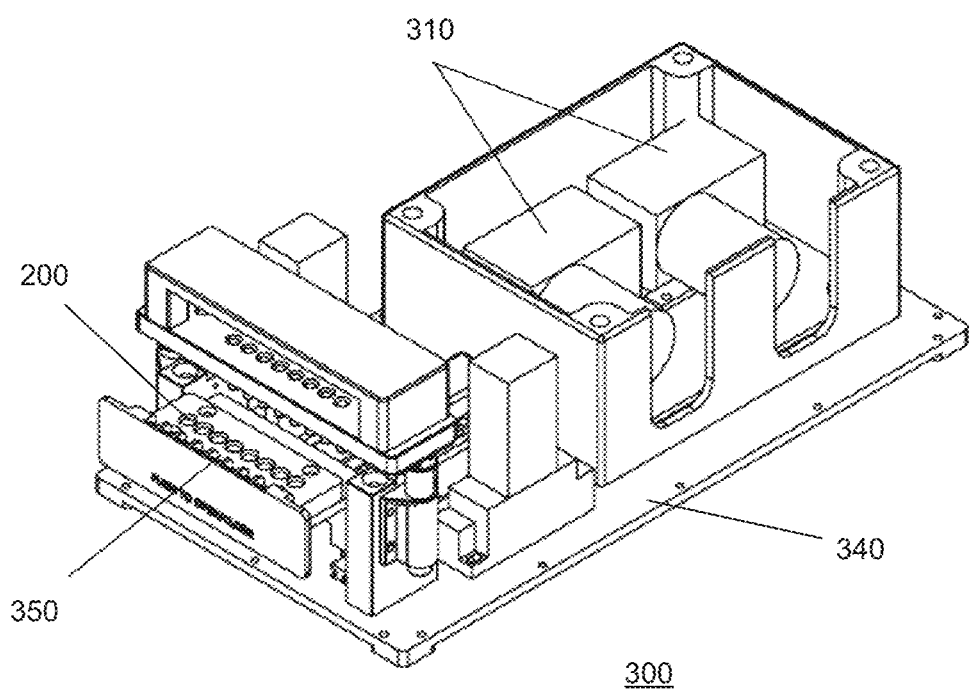
FIG. 4 shows a schematic diagram of a perspective view of the device of FIG. 3 in a packaged form in accordance with another embodiment of the present disclosure.

A schematic diagram of a perspective view of device 300 in a packaged form in accordance with another embodiment of the present disclosure is shown in FIG. 4. The device 300 comprising vacuum pumps 310 is provided on substrate 340 for portability. Holders 200 housing high-density arrays 100 (not shown) are slotted into slidable casing 350 comprising holes sized to receive holders 200. The vacuum pumps 310 are partially enclosed for safety reasons and the various components of device 300 are compartmentalized for ease of use. In use, once holders 200 are placed into casing 350, casing 350 is slid closed. The closed casing 350 is configured such that the open ends of holders 200 are located directly under the respective nozzles 330 (not shown).

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

The invention claimed is:

1. A method of charging an array of micro-capillaries, said micro-capillaries having at least one end that is open for fluid communication, the method comprising the steps of:

(a) filling the array of micro-capillaries with an assay liquid;
    (b) controllably evaporating at least some of the assay liquid to remove it from the micro-capillaries and create a void space in each of said micro-capillaries between the assay liquid and the open end; and
    (c) filling the void space with a liquid that is immiscible with said assay liquid.

2. The method as claimed in claim 1, wherein the evaporating step (b) comprises controlling the rate of evaporation in step (b).

3. The method as claimed in claim 1, wherein the evaporating step (b) comprises a step of passing a gas over the at least one open end of said micro-capillaries.

4. The method as claimed in claim 3, wherein the passing step comprises controlling the flow rate of the gas over the at least one open end of said micro-capillaries.

5. The method as claimed in claim 3, wherein the passing step comprises controlling the duration of the passing step.

6. The method as claimed in claim 1, wherein the evaporating step (b) comprises removing up to 50 vol % of the assay liquid from said micro-capillaries.

7. The method as claimed in claim 3, wherein the gas is air.

8. The method as claimed in claim 4, wherein the passing step comprises a step of pumping air over the at least one open end of said micro-capillaries.

9. The method as claimed in claim 4, wherein the passing step comprises a step of a vacuum pulling air over the at least one open end of said micro-capillaries.

10. The method as claimed in claim 1, wherein the assay liquid comprises an assay reagent.

11. The method as claimed in claim 1, wherein assay liquid in adjacent micro-capillaries comprise the same or different assay reagents.

12. The method as claimed in claim 1, wherein assay liquid in adjacent micro-capillaries comprise components capable of chemically reacting with each other.

13. The method as claimed in claim 1, wherein the immiscible liquid is a mineral oil when the assay liquid is in an aqueous phase.

* * * * *